United States Patent [19]

Heiba et al.

[11] 4,179,392

[45] Dec. 18, 1979

[54] BIODEGRADABLE HARD WATER DETERGENTS

[75] Inventors: El-Ahmadi I. Heiba; Albert L. Williams, both of Princeton, N.J.

[73] Assignee: Mobil Oil Corporation, New York, N.Y.

[21] Appl. No.: 385,623

[22] Filed: Aug. 3, 1973

Related U.S. Application Data

[62] Division of Ser. No. 100,543, Dec. 21, 1970, Pat. No. 3,770,643.

[51] Int. Cl.$^2$ .......................... C11D 9/26; C07C 59/23
[52] U.S. Cl. ........................ 252/108; 252/94;
252/95; 252/99; 252/102; 252/109; 252/110;
252/117; 252/132; 252/531; 252/535;
252/DIG. 1; 252/DIG. 6; 562/537; 562/587;
562/579
[58] Field of Search ............... 252/108, 109, 110, 117,
252/132; 260/413, 535 R; 562/537, 587, 579;
134/42

[56] References Cited

U.S. PATENT DOCUMENTS

| | | | |
|---|---|---|---|
| 2,653,972 | 9/1953 | Ash et al. | 562/537 |
| 3,305,488 | 2/1967 | Osipow et al. | 252/117 |
| 3,468,944 | 9/1969 | Chafetz et al. | 260/514 K |
| 3,741,911 | 6/1973 | Shane et al. | 252/DIG. 1 |
| 3,821,115 | 6/1974 | Lamberti | 252/117 |
| 4,098,818 | 7/1978 | Krummel et al. | 562/587 |

*Primary Examiner*—Leland A. Sebastian
*Attorney, Agent, or Firm*—Charles A. Huggett; Vincent J. Frilette

[57] ABSTRACT

A novel class of biodegradable detergents having improved resistance to precipitation in hard water are the water-soluble ionic salts or nonionic esters or amides of alkanoic acids which are substituted by at least one group containing an electronegative atom, said substitution being attached to a carbon atom 2 to 5 positions from the carboxyl carbon. Gamma-substituted alkanoic acid derivatives are preferred.

3 Claims, No Drawings

BIODEGRADABLE HARD WATER DETERGENTS

CROSSREFERENCE TO COPENDING APPLICATIONS

This application is a division of application Ser. No. 100,543, filed on Dec. 21, 1970, now U.S. Pat. No. 3,770,643.

BACKGROUND OF THE INVENTION

1. Field of the Invention

This invention relates to biodegradable acid derivatives and to the use of such derivatives as highly stable hard water soaps and to liquid and solid detergent compositions containing such derivatives. More specifically, this invention relates to detergents having as the essential ingredient a water-soluble beta- to epsilon-substituted alkanoic acid derivative.

2. Description of Prior Art

It is known in the art to use alkali metal salts of naturally occurring fatty acids, such as sodium salts, as soaps (G. B. No. 1,167,826). Such soaps, while effective detergents under soft water conditions, form precipitates due to the presence of such ions as calcium, magnesium or iron. These precipitates may contribute to the formation of rings around sinks or bathtubs. The detergent ability of any remaining soap in solution is considerably lessened. Other additives are usually added to such detergent compositions to increase both ionic strength for improved solubility and cleaning ability, including such additives as "builders". The commonly used builders are the sodium phosphate and nitrilotriacetate salts. The use of phosphates in detergent and soap compositions are under considerable criticism because they constitute pollutants in rivers and streams. The effect of the nitrilotriacetate salts in natural water courses is presently being reviewed.

Another class of soap is the alkyl benzene sulfonate, having an alkyl group of up to about $C_{20}$. In U.S. Pat. No. 3,296,146, an alkyl benzene sulfonate soap is stated to have improved detergency by the presence of a 2-hydroxyl-1-amino alkane. In U.S. Pat. No. 3,320,174, there is disclosed a detergent composition containing linear alkyl benzene sulfonates, which may also contain other additives, such as lauric diethanolamide or its ethylene oxide derivatives. The difficulty with these benzene sulfonates is that, although they are somewhat biodegradable, they are relatively slower to decompose, possibly because of the benzene ring which is difficult to break down by microbial attack. Moreover, they often require the use of phosphate or nitriloacetate builders for improved detergency. U.S. Pat. No. 3,305,488 describes detergent compositions containing an organic detergent and an alkali metal or ammonium salt of 10-hydroxystearic acid. In combination with synthetic detergents, such as alkyl benzene sulfonates, or derivatives of fatty acids, such as sodium sulfate glyceryl monoesters of fatty acids, these salts are said to improve detergency performance. But the salts are stated to be poor detergents alone in comparison with ordinary stearic acid soaps (col. 3, lines 2.5).

SUMMARY OF THE INVENTION

The detergents of this invention are water-soluble derivatives of substituted alkanoic acids, including salts, amides, and esters, said substitution containing an electronegative atom attached to at least one carbon atoms 2 to 5 positions from the carboxyl carbon.

More specifically, the said derivatives have the following chemical structure:

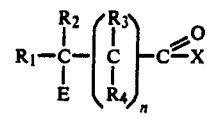

wherein n is an integer of 1 to 4; $R_1$, $R_2$, $R_3$ and $R_4$ may individually be hydrogen or hydrocarbyl having from 1 to 40 carbon atoms, at least one of these being alkyl having at least 2 carbon atoms; E is an oxygen-or sulfur-containing radical or cyano radical, or $R_2$ and E may together be a divalent oxo or imino radical, having a formula weight ranging from 15 to 1600; and X is either an oxygen atom attached to a cation of an alkali metal or ammonium or to an organo group or a nitrogen atom having hydrogen or one to two organo groups attached thereto, all of the various R substituents rendering the derivative water soluble.

DESCRIPTION OF PREFERRED EMBODIMENTS

More particularly, the $R_1$, $R_2$, $R_3$ and $R_4$ radicals may individually be hydrogen or hydrocarbyl, such as alkyl, alkylene, and oxy, amino or hydroxy derivatives thereof, including such groups as hydroxylalkyl and hydroxyalkenyl or ether radicals, i.e., alkoxyalkyl, having from 1 to about 40 carbon atoms, and at least one of the above radicals, preferably $R_1$ or $R_2$ is an alkyl radical of at least 2 carbon atoms. Each of $R_1$, $R_2$, $R_3$ and $R_4$ may be the same or different. If partial biodegradability is acceptable, these radicals may include aromatic groups such as aryl, alkaryl and aralkyl. Of particular interest in this invention are the acid chains in which n in the above structure is 2, $R_1$ is an alkyl or alkenyl radical having from 4 to about 30 carbon atoms, preferably 5 to 26, and $R_2$, $R_3$ and $R_4$ are hydrogen. The most preferred soaps, therefore, are derivatives of gamma-substituted acids, such as octanoic, nonanoic, decanoic, undecanoic, dodecanoic, tridecanoic, tetradecanoic, pentadecanoic, hexadecanoic, octadecanoic, eicosanoic, and the like.

The group E is an electronegative substituent which contains an oxygen or sulfur linkage or cyano. Thus, E includes such groups as hydroxy, alkoxy, hydroxyalkoxy, alkoxyalkoxy, cyano, alkylthio, thiocyano, alkali metal sulfonato and alkali metal sulfato. $R_2$ and E may also be a combined divalent radical such as imino or oxo, resulting in an iminoacid or ketoacid. If desired, E also may contain an aromatic group, e.g. phenoxy, tolyloxy, benzyloxy. The organo portion of the E radical may contain from 1 to about 40 carbon atoms. Such groups include ethers obtained from olefin oxides, such as ethylene or propylene oxide, or alkylene glycols including polyalkylene glycols, such as polyethylene or polypropylene glycol, having formula weights of up to 1000, preferably up to 800. The most preferred group for E is hydroxy. However, the other named substituents whether obtained directly from preparation of the acid derivative or derived from the hydroxy substituent by subsequent reaction with known reagents also provide desirable detergents.

The detergents of this invention include both ionic and nonionic derivatives. For ionic soaps, the radical X of the formula is —OX' wherein X' may be an alkali metal, preferably sodium, potassium and lithium, or ammonium. The ammonium radical may have hydrogen atoms or be further substituted by 1 to 4 organic groups, such as alkyl groups, each having from 1 to 10 carbon atoms and hydroxy and amino derivatives thereof. For nonionic soaps, X may have either of the following structures

—OX'' or

wherein X'' and X''' may each be aliphatic hydrocarbyl, such as alkyl or alkenyl, having from 1 to 20 carbon atoms. As in the previous R groups, X'' and X''' may contain aryl, alkaryl or aralkyl radicals, if desired. At least one X''' may also be hydrogen, or hydroxy- or amino-containing organic radicals of the structure —($C_aH_{2a}Y)_b$H, in which a is 2 to 5, b is 1 to 20, and Y is oxygen or secondary amino, and, when b is greater than 1, each Y may be the same or different. Thus the formula weight of X'' or X''' may range up to about 1700, preferably up to 800. Representative of such groups for X'' and X''' are ethyl, propyl, butyl, hydroxyethyl hydroxypropyl, aminoethyl, aminopropyl, ethoxyethyl, propoxypropyl, ethylaminoethyl, propylaminopropyl, N,N-bis (hydroxyethyl)aminoethyl, polyethylene glycol ethyl ether, polypropylene glycol propyl ether and the like. As in the case of E, X''' may also contain sulfato and sulfonato groups, as the acyl taurides, and, with an additional carboxyl group, N-acyl sarcosinates.

From the above discussion it may be seen that the preferred detergents of this invention are of a class of water-soluble alkali metal or ammonium salts or amides or esters of a class of hydroxyalkanoic acids having from 8 to about 36 carbon atoms.

When X is represented by an ionic group, it is most preferred that $R_1$ be an alkyl group containing from 5 to 14 carbon atoms and $R_2$, $R_3$ and $R_4$ are hydrogen. When X is a nonionic group, the $R_1$, $R_2$, $R_3$ and $R_4$ substituents may contain a considerably greater number of carbon atoms as previously defined. Accordingly the compounds representing the preferred ionic soaps of this invention include the alkali metal or ammonium salts of gamma-hydroxy ($C_8$-$C_{20}$) alkanoic acids: gamma-hydroxyoctanoic acid, gamma-hydroxynonanoic acid, gamma-hydroxydecanoic acid, gamma-hydroxydodecanoic acid, gamma-hydroxytetradecanoic acid, gamma-hydroxypentadecanoic acid, gamma-hydroxyoctadecanoic acid, gamma-hydroxynonadecanoic and gamma-hydroxyeicosanoic acid. The preferred nonionic soaps of this invention are represented by the alkanol amides, e.g. amides, diethanolamide, monoethanolamide and their tauride derivatives, the glycol esters, e.g. ethylene glycol ester, polyglycol ester, e.g. octaethylene glycol, and the esters of trialkanolamines, e.g. triethanolamine, of the 3- to 6-hydroxy acids.

The detergents of this invention are preferably obtained by opening the ring of substituted lactones of the beta, gamma, delta, or epsilon type, in which carbon atoms in the lactone ring may have attached the substituents $R_1$, $R_2$, $R_3$ and $R_4$ above described. The desired lactone precursor may be obtained by generally known techniques which are not part of the present invention. Substituents may be attached to a lactone by reacting the lactone with one or more olefins or with an aldehyde. Maleic anhydride may be reacted with an olefin to produce an alkenyl-substituted succinic anhydride which upon selective reduction produces an alpha- or beta-alkyl substituted gamma-lactone.

In our preferred method, an unsaturated compound, such as an olefin, is reacted with a carboxylic acid in the presence of a metal ion, such as manganese. This reaction is referred to in a copending application Ser. No. 30,582, filed on Apr. 21, 1970 now abandoned, and continuation-in-part application thereof Ser. No. 336,857 filed Feb. 28, 1973. If a 1-olefin is reacted with acetic acid, a gamma-hydrocarbyl-gamma-butyrolactone is produced. If the unsaturated bond of the olefin is internal, the butyrolactone would have a beta, gamma-substitution, the two carbon atoms of the unsaturated bond becoming the beta and gamma carbons of the lactone. If a carboxylic acid other than acetic is used, e.g. propionic, the resulting lactone would have an alpha-substituent, in this case, methyl. The preferred lactone contains an alkyl group of at least 2 carbon atoms in the gamma position. If desired, mixed unsaturated compounds or mixed carboxylic acids may be used in the reaction to produce a mixture of mixed substituted lactones, which mixture may then undergo ring opening to produce a useful detergent mixture.

The opening of the lactone ring may be carried out, e.g. by mixing the lactone with an alkali metal hydroxide. The following sequence illustrates a typical reaction used in preparing the ionic soaps of this invention.

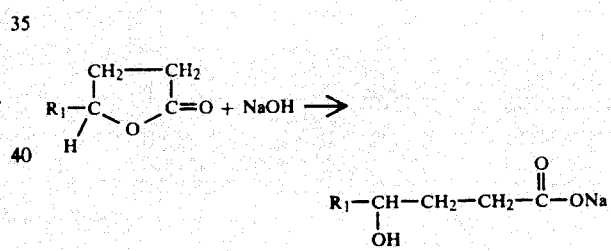

The other alkali metal hydroxides or the ammonium hydroxide may also react in the same way. Reaction with ammonia may require a two-step procedure in which the ring is opened with an alkaline earth hydroxide, such as barium hydroxide. The resulting barium salt is then reacted with ammonium compound such as ammonium carbonate. In one modification of this invention, the alkali metal or ammonium soap of this invention may be further reacted with an olefin oxide, such as ethylene oxide or propylene oxide, to produce the corresponding ester. By reacting the soap with excess olefin oxide under suitable reaction conditions, the olefin oxide can also react with the substituent on the acid chain (E in the aforementioned formula). When E is hydroxy, the ether would be formed. Such ester and ester-ether derivatives are useful detergents.

The lactone may also be reacted with an amine or polyamine to produce the corresponding amide or with an alcohol or polyol to produce the corresponding ester. However, it may be necessary to add a small amount of an alkali metal alkoxide of a lower alkyl ($C_1$ to $C_6$) alcohol or a mineral acid, such as hydrochloric or sulfuric, to aid in the opening of the lactone ring.

The amines useful to prepare detergents of this invention include both alkylamines, and alkanolamines and polyamines of the formula $H_{3-c}-N-[(C_aH_{2a}Y)_bH]_c$ wherein integer a is from 2 to 5, b from 1 to 20 and c from 1 to 3, and Y is either oxygen or secondary amine and the various X groups may be the same or different when b is greater than 1. It is believed that this reaction may also permit interreaction between the carboxyl and an unreacted hydroxy or amine group of the resulting amide, producing a small amount of the corresponding oxazoline or imidazoline in the reaction mixture. A molecule of water is removed. In fact, if so desired, the amide-containing reaction mixture may be further heated at reflux, or from 100° to 300° C. to remove water, thereby producing any of these heterocyclic products. Such products also have utility as detergents, textile treating agents and the like. If the nitrogen atom of the imidazoline is further quaternized with an organic salt of a mineral acid, such as methyl sulfate, the resulting products are useful as textile softeners. Hence, the reaction mixtures of reactions between the lactone and an alkanolamine or alkylenepolyamine are within the scope of this invention, wherein the presence of the oxazoline or imidazoline derivative of the substituted synthetic acid amide could occur.

In another procedure, an aldehyde, $R_1CHO$, is reacted with maleic acid or ester thereof, i.e. dimethyl, carbon dioxide is removed to produce a keto acid ($R_2$ and E are combined as oxo) which, upon conversion to the salt, ester or amide, provides a detergent within the scope of this invention.

As stated previously, many ionic soaps do not remain in solution in water during use because of the hardness of the water. Hence as an aid in keeping these conventional soaps in solution, formulators have had to add to the detergent composition certain builders which are not readily biodegradable, resulting in a waste disposal problem, especially by adversely affecting the ecological balance of our natural waterways. For example, phosphate types overstimulate algae growth, the subsequent decay of which consumes considerable oxygen necessary for aquatic life in the water.

Ordinarily, these builders are present to a significant extent, usually ranging from 25% to over 50% by weight of commercial detergent compositions. We have found that the detergents of this invention have such markedly improved resistance to the effect of hard water and such high detergent qualities that they can be used without any additional builders. Yet the detergents of this invention are compatible with such additives. In certain instances, such builders can be tolerated to a limited concentration. Accordingly, in the detergent compositions of this invention, builders may be either completely omitted or may be added to an extent of up to 20% by weight of total detergent composition. Such builders include sodium tripolyphosphate, sodium pyrophosphate, trisodium phosphate, nitrilotriacetic acid sodium salt and the like.

Other adjuvants besides builders normally found in detergent compositions may be present in the detergent compositions of this invention. These include sequestering agents, germicides, fungicides, perfumes, bleaches, and optical whiteners, specifically alkali metal salts such as sodium metaborate, sodium tetraborate, sodium perborate, sodium silicate, sodium carbonate, sodium sulfate, sodium acetate, sodium propionate and the like. Preferred are the alkali metal salts of 2- to 6-carbon carboxylic acids. Other additives, such as starches, tallow soaps and the like, are useful in preparing detergents in different forms.

The detergents of this invention may also be mixed with known conventional detergents, such as salts and amides of natural fatty acids, and other known soap detergents, such as alkyl glyceryl ether sulfonates; alkyl sulfates, alkyl monoglyceride sulfates or sulfonates; alkyl polyethenoxy ether sulfates; acyl sarcosinates; acyl N-methyl taurides; alkylbenzenesulfonates; alkyl phenol polyethenoxy sulfonates. In these compounds the alkyl and acyl groups may contain from 10 to about 20 carbon atoms. They are used in the form of water-soluble salts, the sodium, potassium, ammonium, and alkyl ammonium salts, for example. Specific examples are: sodium lauryl sulfate; potassium N-methyl lauroyl tauride; triethanolammonium dodecylbenzene sulfonate.

The examples of nonionic organic detergents which can be used in the compositions of this invention if desired are: polyethylene oxide condensates of alkyl phenols wherein the alkyl group contains from 6 to 12 carbon atoms (e.g. t-octylphenol and the ethylene oxide is present in a molar ratio of ethylene oxide to alkyl phenol in the range of 10:1 to 25:1; condensation products of ethylene oxide with the product resulting from the reaction of propylene oxide and ethylene diamine wherein the molecular weight of the condensation products ranges from 5,000 to 11,000; the condensation products of from 5 to 30 moles of ethylene oxide with one mole of a straight or branched chain aliphatic alcohol containing from 8 to 18 carbon atoms (e.g. lauryl alcohol); $C_{10}$-$C_{18}$ alkyl di-1($C_1$14 $C_2$ alkyl) amine oxides (e.g. dodecyl dimethyl amine oxide). The resulting detergent mixture then may be modified by addition of limited amount of builders. As stated previously, such as nitrilotriacetic acid sodium salt and trisodiumpolyphosphate, and by softeners, odorants, and optical brighteners, to produce an acceptable commercial product. In any case, it is desirable that at least about 2% of the synthetic, modified, alkanoic acid detergent derivative of this invention be present in the final mixture, and preferably that at least 5% to 75% of the final composition be constituted of the improved soaps or detergents of this invention.

It should be also noted that products of this invention are considered novel. In particular, such products include amides, alkanolamides, dialkanolamides, the salts and esters of the substituted alkanoic acids in which $R_1$ of the aforementioned formula is alkyl of 4 to 30 carbon atoms and X is an ammonium-oxygen group or an ester radical. Preferably, X is derived from an alkylene glycol, such as polyethylene glycol or trialkanolamine, such as triethanolamine, or a tetraalkylammonium compound, such as tetramethylammonium hydroxide or ammonia or substituted ammonia such as diethanolamine.

The following examples are presented for a purpose of illustrating this invention and are not intended to constitute any limitation thereof.

EXAMPLE 1

A three liter 4-neck flask is fitted with a reflux condenser having a nitrogen inlet tube at the top, a stirrer, dropping funnel, and thermometer. Into the flask are added 558 grams (9.3 moles) of acetic acid and 91.9 grams (0.439 mole) of manganous acetate dihydrate, with stirring and heating under nitrogen. When the temperature reaches 90° C., 16.5 grams (0.104 mole) of solid potassium permanganate is added. When the temperature is again at 90° C., 76.7 grams (0.751 mole) of acetic anhydride is added. After the temperature rise ceases and drops 3°, 44.0 grams (0.312 mole) of decene-1 is introduced, followed by 250 grams of sodium acetate. The reaction mixture is heated to reflux, at 134° C. pot temperature. After 2 hours of reflux under nitrogen, the mixture has a clear yellow color. To the reaction mixture is added one liter of water. The crude product is extracted with 200 ml of benzene, and the aqueous layer washed with 100 ml of benzene. Benzene is distilled from the combined extracts leaving 55.1 grams of the resulting product from which the decene-1 is removed by vacuum distillation. The lactone is distilled at 90° C. and 0.5 mm Hg. The yield of gamma-(n-octyl)-gamma-butyrolactone is 34.1 grams (66% of theory) of an oily, colorless liquid.

EXAMPLE 2

In a 2-liter flask under a nitrogen atmosphere, 25.8 grams (0.48 mole) of sodium methoxide is suspended in 250 ml of benzene at 10° C. with stirring. To this suspension 59.5 grams (0.692 mole) of gamma-butyrolactone is added. This is followed by the addition of 44.4 grams (0.346 mole) of n-octanal. The temperature reaches a maximum of 30° C. The mixture is stirred under nitrogen for four hours at 25° C., and then acidified with dilute (6 N) sulfuric acid. The aqueous layer is separated and washed with 100 ml of benzene, and the washings added to the remaining benzene layer. The resulting benzene layer is washed with three 1-liter portions of water, and the benzene is evaporated under nitrogen. The remaining residue of 63.6 grams is placed in a standard hydrogenation bottle along with 0.1 grams of platinic oxide catalyst. Hydrogenation at 40–50 lb. pressure is continued until uptake of hydrogen ceases. The catalyst is filtered off, and the crude product vacuum distilled at 90° C. and 0.5 mm Hg. The fraction of alpha-(n-octyl)-gamma-butyrolactone distilling at 120°–122° C. weighs 22.7 grams.

EXAMPLE 3

A solution of 4.131 grams (0.1007 mole) of sodium hydroxide (analysis; 97.5%) in 60 ml of 95% ethanol is prepared by heating together in a one-neck 300 ml flask under a reflux condenser. To the flask are added 20.028 grams (0.1010 mole) of gamma-(n-octyl)-gamma-butyrolactone and washed in with 10 ml of 95% ethanol. The mixture is brought to reflux and refluxed for two hours. The ethanol is then distilled off at reduced pressure to leave a residue of 24.1 grams of crude product. This residue is extracted with 100 ml of n-hexane at reflux for 1 hour. The hexane is filtered off, and the residue again extracted by 200 ml of refluxing n-hexane. When the second portion of hexane has been removed by filtration, the product is dried under vacuum at 50° C. for 16 hours. The yield of white crystals of the purified sodium gamma-hydroxydodecanoate is 22.5 grams (94.5% yield).

EXAMPLE 4

Into a similar reactor as that used in Example 3 are added 10.51 grams (0.10 mole) of diethanolamine and 9.05 grams (0.04 mole) of gamma-decyl-gamma-butyrolactone, prepared in a manner similar to that described in Example 1, except dodecene-1 is used instead of decene-1, and 0.05 gram sodium methoxide. The mixture is heated and stirred at 150° C. for 7 hours. Then additional sodium methoxide (0.05 gram) is added. After 25 hours at 150° C., additional diethanolamine (10.51 grams, 0.100 mole) and sodium methoxide (0.05 grams) are added. After 54 hours, the reaction is complete, yielding almost quantitative yield of the diethanolamide of gamma-hydroxytetradecanoic acid.

EXAMPLE 5

Into a similar reactor as used in Example 3 are added 20.0 grams of polyethylene glycol (0.0500 mole; molecular weight range 380–420, average 400), 5.66 grams (0.0250 mole), of gamma-decyl-gamma-butyrolactone, 0.50 gram of sulfuric acid and 20 ml of xylene. The mixture is refluxed for several hours during which time 1.6 ml of water is removed azeotropically with xylene. To the resulting mixture is added 1.0 gram of calcium oxide. The product is filtered and evaporated to give 22.74 grams of product. This product is treated with charcoal in methanol to give 21.57 grams of colorless waxy product which is the polyethylene glycol ester of gamma-(polyethylene glycol ether) tetradecanoic acid. This product has good detergent properties.

EXAMPLE 6

The same procedure as used in Example 5 is followed, except 10.0 grams of polyethylene glycol (0.025 mole) is added. The resulting product, the glycol ester of gamma-hydroxytetradecanoic acid, evidences good cleaning properties.

EXAMPLE 7

Using a similar procedure as in Example 3, a solution of sodium hydroxide in ethanol is mixed with epsilon-hexylepsilon-hexanolactone in equimolar amounts. The mixture is refluxed for three hours, and ethyl alcohol is distilled in vacuo. The residue is extracted twice with n-hexane under reflux, and the n-hexane is removed. The resulting solid product is dried under vacuum. This product has good detergent properties.

EXAMPLE 8

Using a similar procedure as in Example 1, undecene-2 is reacted with propionic anhydride in the same molar ratio as used in that example. The crude product is refined in a similar manner as described in Example 1. The yield of product alpha-methyl-beta-methyl-gamma-octylbutyrolactone and its isomeric homologue alpha-methyl-beta-octyl-gamma-methylbutyrolactone is about 50% of theory. Upon hydrolysis with sodium hydroxide in accordance with the procedure of Example 3, the resulting sodium salts of the corresponding hydroxydodecanoic acids has satisfactory detergent properties.

EXAMPLE 9

Following the procedure of Example 1, a mixture of decene-1 and hexadecene-1, at a mole ratio 2:1, respectively, is reacted with acetic acid, in which the ratio of total moles of the combined olefins to the acetic acid is the same as the olefin-acid mole ratio in the Example 1. The reaction mixture is treated in the same manner as the product in Example 1. The resulting product is mixed with sodium hydroxide under the conditions described in Example 3 to produce the sodium soaps of gamma-hydroxydodecanoic acid and gamma-hydroxyoctadecanoic acid. This mixture of soaps has good detergent properties.

EXAMPLE 10

Following the procedure of Example 4, monoethanolamine is used in the reaction (instead of diethanolamine) with the same mole ratio of reactants, as in Example 4. The resulting product is mixed with xylene and refluxed to remove water azeotropically. The resulting reaction mixture is mixed at a concentration of 10% by weight in water with carboxymethyl hydroxyethyl cellulose at 0.5% and sodium acetate at 3.5%. This liquid mixture has good detergent properties.

EXAMPLE 11

In a suitable reactor, 25.0 grams (0.097 mole) of dimethyl alpha-(n-heptanoyl) succinate is mixed with 300 ml of 1 N. hydrochloric acid and heated at reflux for 20 hours. The solid which separates upon cooling is filtered off, and then dissolved in 100 ml of benzene. The product is extracted into 200 ml of 5 N. sodium hydroxide solution, and separated from the benzene. Free acid is liberated by acidification of the aqueous solution, using 6 N. hydrochloric acid. Liberated free acid is extracted into two 100 ml portions of benzene. Evaporation of the benzene under vacuum leaves 14.2 g of 4-ketodecanoic acid. This acid is heated with 3.0 g of sodium hydroxide (98.8%) in 400 ml of 95% ethyl alcohol, and 300 ml of alcohol are distilled off. The remainder of the alcohol is removed under vacuum to leave dry salt. The salt is extracted by 300 ml of n-hexane, and filtered off to leave a quantitative yield of sodium 4-ketodecanoate, based on sodium hydroxide. This white product has good detergent properties even in hard water.

EXAMPLE 12

Using the procedure of Example 3, 13 g of a 25% aqueous solution of tetramethylammonium hydroxide is allowed to react with 6.79 grams of gamma-n-decyl-gamma-butyrolactone. After removal of water and extraction by n-hexane, a quantitative yield of purified tetramethylammonium gamma-hydroxytetradecanoate is obtained. This white solid product has good detergent properties even in hard water.

EXAMPLE 13

Using the procedure of Example 3, 8.20 g of barium hydroxide octahydrate in 100 ml of water is mixed with 4.96 g of gamma-n-decyl-gamma-butyrolactone in 50 ml of ethyl alcohol. The resulting solution is then diluted with 200 ml of warm water. This dilute solution is then titrated with a 13% solution of aqueous ammonium carbonate until precipitation ceases. The precipitate is filtered off. Evaporation of the solvents from the filtrate leaves a quantitative yield of ammonium gamma-hydroxytetradecanoate. This white solid product has good detergent properties even in hard water.

EXAMPLE 14

A. In a reactor similar to that used in Example 3, polyethylene glycol (average molecular weight 400) is refluxed with a mixture of benzene and potassium tert-butoxide. After one half hour of refluxing the mixture, gamma-decyl-gamma-butyrolactone in an amount molar equivalent to the polyethylene glycol is added to the reactor. The resulting mixture is allowed to reflux an additional one half hour. Additional amounts of potassium tert-butoxide are added until all of the lactone is reacted (the disappearance of the lactone is followed by gas chromotography during the procedure). The resulting mixture is filtered hot and the benzene distilled off under vacuum. A white semi-solid product, the potassium salt of gamma-poly(ethylene glycol) ether tetradecanoic acid, is obtained. Analysis shows this to be the salt of a carboxylic acid (infra-red absorbtion 6.35 microns).

B. Gamma-octyl-gamma-butyrolactone is mixed with the preformed sodium salt of the same polyethylene glycol used in A in the presence of tetrahydrofuran. The mixture is heated to reflux for about an hour. The tetrahydrofuran is evaporated off leaving the sodium salt of gamma-poly(ethylene glycol) ether dodecanoic acid in a yield of over 95% of theory.

Both products made in this example show good detergent properties.

The excellent detergent properties and resistance to precipitation in hard water of the synthetic, modified alkanoic acid derivatives of this invention, even in absence of conventional builders and sequestrants, are demonstrated in a series of washing tests. The tests are made in a Terg-O-Tometer Model 7243, manufactured by United States Testing Company, Inc. of Hoboken, N.J., using a test procedure essentially as recommended by United States Testing. Several sodium salts of gamma-hydroxy acids are used by adding 0.3 gram to a liter of water having a hardness of 100 ppm. as $CaCO_3$. Soiled cloths with an average reflectance of 67% are cleaned by essentially the following procedure: the cloth is placed in a 2-liter stainless steel beaker with the soap solution at about 120° F. and agitated by an impeller at 110 cycles per minute for 15 minutes; the cloths are rinsed in the same hard water for from 2 to 5 minutes. After drying the cloths are measured for reflectance in a reflectance meter which reads percent of reflected light, using magnesium oxide as 100% reflectance. The increased reflectances of the cleaned cloths and the presence or absence of precipitate in the detergent solution are as follows:

| Detergent | % | Precipitate | Increased Reflectance, % |
|---|---|---|---|
| Sodium salt of gamma-hydroxydecanoic acid | 0.03 | None | 6.0 |
| Sodium salt of gamma-hydroxydodecanoic acid | 0.03 | None | 5.3 |
| Sodium salt of gamma-hydroxytetradecanoic acid | 0.03 | Light | 4.4 |
| Diethanolamide of gamma-hydroxytetradecanoic acid | 0.03 | None | 7.9 |
| Monoethanolamide of gamma-hydroxytetradecanoic acid | 0.03 | Medium | 5.8 |
| Ethoxylated gamma-hydroxytetradecanoic acid | 0.03 | None | 7.2 |

Further tests made in the standard Terg-O-Tometer show the superiority of the detergents of this invention over similar compounds and also a commercial detergent. These tests are performed upon a more heavily soiled standard cloth obtained from the United States Testing Company, Inc. This cloth has initial reflectance of only 27.0%. Washing with water alone increases this to only 28.5%. Performances of detergents with and without sodium tripolyphosphate builder (STPP) in water having a hardness of 100 ppm as $CaCO_3$ are as follows:

| Detergent | % by weight of Active Agent | Increased Reflectance, % |
|---|---|---|
| None | 0 | 5.5 |
| Diethanolamide of gamma-hydroxytetradecanoic acid | 0.050 | 42.3 |
| Diethanolamide of gamma-hydroxytetradecanoic acid | 0.075 | 42.3 |
| Diethanolamide of tetradecanoic acid | 0.050 | 18.2 |
| Diethanolamide of tetradecanoic acid | 0.075 | 18.9 |
| Diethanolamide of gamma-hydroxytetradecanoic acid plus 0.041% STPP | 0.050 | 47.0 |
| Diethanolamide of tetradecanoic acid plus 0.041% STPP | 0.050 | 32.2 |
| LAS* | 0.050 | 32.6 |
| Standard LAS, built formula (has 15% LAS)** | 0.50 | 37.0 |
| Standard LAS, built formula (has 15% LAS)** | 1.00 | 37.8 |

*Linear alkyl benzene sulfonate (up to about $C_{15}$-alkyl)
**Mixture of 15% linear alkyl benzene sulfonate (85% assay Sulframin LX flakes), 35% sodium tripolyphosphate and 50% sodium sulfate (anhydrous basis)

The diethanolamide of tetradecanoic acid and its gamma-hydroxy counterpart both have maximum increased reflectance when at 0.05%. Higher concentration does not increase their effectiveness. At either concentration, however, the hydroxy acid amide is much more effective than the non-hydroxy counterpart. The presence of the STPP builder increases the reflectance of both, but the hydroxyacid amide is still a much more effective detergent. The hydroxyacid amide also provides a much higher reflectance than the linear alkylbenzene sulfonate (LAS) at the same concentration. It is also more effective than LAS at three times the concentration (0.15%) in the presence of a large concentration of builder (0.35%), where the concentration of the total built formula is 1.00%.

We have found that the suds formation of the soaps of this invention are stable even in very hard water. In the following test, various solutions of sodium salts of several gamma-hydroxy acids dissolved in distilled water are shaken with 65 grams of 40 to 100 mesh limestone. The length of time of the shaking period after which suds still form is measured. The results are as follows:

| Sodium Salt of | Concentration Salt in Solution-Weight % | Length of Time of Shaking With Suds Formation |
|---|---|---|
| Gamma Hydroxyoctanoic Acid | 0.01 | over 4 days* |
| Gamma-hydroxydecanoic Acid | 0.001 | over 7 days* |
| Gamma-hydroxydodecanoic Acid | 0.001 | over 4 days* |
| Octadecanoic Acid | 0.1 | less than 1 hour |

*Test discontinued; suds still being formed.

The results of this test indicate that the derivatives of this invention may have utility in the water-flooding of oil wells useful in increasing oil production; many agents presently contemplated for use in water-flooding operations tend to precipitate out of solution when in contact with the limestone normally found near petroleum deposits.

The detergents of this invention are also found to have rust inhibiting properties. The sodium salt of gamma-hydroxydodecanoic acid added to a metal cutting fluid formulation reduces rust formation.

The synthetic or modified fatty acid derivatives of this invention may be formulated as detergents in the usual manner and by way of illustrations thereof the following examples are given:

| Spray-Dried Granular Detergent | Percent |
|---|---|
| Mixture of sodium salts of gamma-hydroxyoctanoic acid, gamma-hydroxytetradecanoic acid and gamma-hydroxydodecanoic acids | 10 |
| Sodium (cracked wax) benzene sulfonate | 10 |
| Sodium tripolyphosphate | 15 |
| Sodium nitrilotriacetate | 10 |
| Sodium silicate | 30 |
| Sodium acetate | 25 |
| Granular Detergent | |
| Sodium salt of epsilon-hydroxydodecanoic acid | 10 |
| Condensation product of one mole of nonyl phenol and nine moles of ethylene oxide | 10 |
| Tetrasodium pyrophosphate | 50 |
| Sodium carbonate | 3 |
| Trisodium phosphate | 3 |
| Sodium sulfate | 24 |
| Milled Toilet Bar(1) | |
| Sodium salt of gamma-hydroxydodecanoic acid | 25 |
| Sodium tallow soap | 60 |
| Water | 15 |
| Milled Toilet Bar(2) | |
| Sodium soap of lactone made by condensing $C_8$—$C_{14}$ olefins, from wax cracking, with acetic acid | 50 |
| Tallow fatty acid soap | 25 |
| Water | 15 |
| Cornstarch | 5 |
| Triethanolamine ethylenediamine tetraacetate | 5 |
| Scouring Cleanser | |
| Silica flour | 85 |
| Detergent consisting of 85% trisodium phosphate and 15% sodium salt of gamma-hydroxyoctanoic acid | 15 |
| Liquid Detergent | |
| Diethanolamide of gamma-hydroxydodecanoic acid | 10 |
| Carboxymethyl hydroxyethyl cellulose | 0.5 |
| Sodium silicate | 3.5 |
| Water | balance |
| Heavy Duty Household Laundry Detergent | |
| Diethanolamide of gamma-hydroxyhexadecanoic acid | 12 |
| Nitrilotriacetic Acid | 10 |
| Sodium Metasilicate | 5.5 |
| Carboxymethyl Cellulose | 0.5 |
| Sodium Carbonate | 72 |

While certain specific examples and preferred modes of practice of the invention have been herein set forth, it will be understood that this is solely for the purpose of illustration and that various changes and modifications may be made without departing from the spirit of the disclosure and the scope of the appended claims.

I claim:

1. A detergent composition consisting essentially of a water soluble derivative of an alkanoic acid having a polyethylene glycol ether substituent attached to a carbon atom 2 to 5 positions from the carboxyl carbon, said polyethylene glycol containing 1 to 20 ethylene oxide residues, said derivative selected from the group consisting of alkali metal salts and ammonium salts of the said substituted alkanoic acid.

2. A detergent composition consisting essentially of the sodium or ammonium salt of 4-hydroxy tetradecanoic acid or 4-hydroxy eiconsanic acid.

3. The method of cleaning a surface by the step of applying to said surface an aqueous solution containing a detergent composition consisting essentially of a water soluble derivative of an alkanoic acid having a polyethylene glycol ether substituent attached to a carbon atom 2 to 5 positions from the carboxyl carbon, said derivative selected from the group consisting of alkali metal salts and ammonium salts of the said substituted alkanoic acid.

* * * * *